US008007827B2

(12) United States Patent
Han et al.

(10) Patent No.: US 8,007,827 B2
(45) Date of Patent: *Aug. 30, 2011

(54) PHARMACEUTICAL DOSAGE FORMS HAVING IMMEDIATE RELEASE AND/OR CONTROLLED RELEASE PROPERTIES

(75) Inventors: Chien-Hsuan Han, Sunnyvale, CA (US); Larry Hsu, Los Altos Hills, CA (US); Ann F. Hsu, Los Altos Hills, CA (US)

(73) Assignee: Impax Laboratories, Inc., Hayward, CA (US)

( * ) Notice: Subject to any disclaimer, the term of this patent is extended or adjusted under 35 U.S.C. 154(b) by 752 days.

This patent is subject to a terminal disclaimer.

(21) Appl. No.: 11/239,249

(22) Filed: Sep. 30, 2005

(65) Prior Publication Data

US 2006/0057197 A1    Mar. 16, 2006

Related U.S. Application Data

(63) Continuation-in-part of application No. 11/138,008, filed on May 26, 2005, now abandoned, and a continuation-in-part of application No. 10/815,924, filed on Apr. 2, 2004, now abandoned, and a continuation-in-part of application No. 10/815,926, filed on Apr. 2, 2004, now abandoned, and a continuation-in-part of application No. 10/815,929, filed on Apr. 2, 2004, now abandoned, and a continuation-in-part of application No. 10/815,930, filed on Apr. 2, 2004, now abandoned.

(51) Int. Cl.
*A61K 9/22*      (2006.01)

(52) U.S. Cl. ......... 424/468; 424/400; 424/457; 424/489

(58) Field of Classification Search .................. None
See application file for complete search history.

(56) References Cited

U.S. PATENT DOCUMENTS

| | | | |
|---|---|---|---|
| 3,080,294 A * | 3/1963 | Shepard ........................ 424/498 |
| 4,497,826 A * | 2/1985 | Narabayashi et al. ........ 514/567 |
| 4,764,380 A | 8/1988 | Urquhart et al. |
| 4,780,463 A * | 10/1988 | Sunshine et al. ............ 514/226.5 |
| 4,968,508 A * | 11/1990 | Oren et al. .................... 424/468 |
| 4,996,058 A | 2/1991 | Sinnreich |
| 5,091,184 A * | 2/1992 | Khanna ........................ 424/435 |
| 5,133,974 A | 7/1992 | Paradissis et al. |
| 5,202,128 A | 4/1993 | Morella et al. |
| 5,217,720 A | 6/1993 | Sekigawa et al. |
| 5,229,131 A | 7/1993 | Amidon et al. |
| 5,651,985 A | 7/1997 | Penners et al. |
| 5,719,185 A | 2/1998 | Bountra et al. |
| 5,840,329 A | 11/1998 | Bai |
| 6,068,859 A | 5/2000 | Curatolo et al. |
| 6,110,494 A | 8/2000 | Clancy et al. |
| 6,156,343 A | 12/2000 | Morita et al. |
| 6,228,398 B1 | 5/2001 | Devane et al. |
| 6,248,363 B1 * | 6/2001 | Patel et al. .................... 424/497 |
| 6,294,200 B1 * | 9/2001 | Conte et al. .................. 424/472 |
| 6,350,769 B1 | 2/2002 | Kaufman et al. |
| 6,455,527 B2 * | 9/2002 | Tulshian et al. .............. 514/249 |
| 6,544,998 B2 | 4/2003 | Mylari |
| 6,627,223 B2 | 9/2003 | Percel et al. |
| 6,645,524 B2 | 11/2003 | Midha et al. |
| 6,664,069 B1 | 12/2003 | Andrews et al. |
| 6,669,957 B1 | 12/2003 | Laruelle et al. |
| 6,692,769 B1 | 2/2004 | Ishibashi et al. |
| 2002/0091250 A1 * | 7/2002 | Kaupmann et al. .......... 536/23.5 |
| 2003/0021845 A1 * | 1/2003 | Friedman et al. ............. 424/470 |
| 2003/0104062 A1 | 6/2003 | Berner et al. |
| 2003/0142035 A1 | 7/2003 | Goldstein |
| 2003/0228360 A1 | 12/2003 | Han et al. |
| 2006/0210631 A1 | 9/2006 | Patel et al. |
| 2006/0246134 A1 | 11/2006 | Venkatesh |
| 2007/0265343 A1 | 11/2007 | Dharmadhikari et al. |
| 2007/0292510 A1 | 12/2007 | Huang |

FOREIGN PATENT DOCUMENTS

WO    WO 03/101432 A1    12/2003

OTHER PUBLICATIONS

Aisen et al., 15(4) Journal of the American Paraplegia Society 211-216 (1992).
Balerio et al., 27(7) Gen. Pharmac. 1269-1271 (1996).
Balerio et al., 27(3) European Journal of Drug Metabolism and Pharmacokinetics 163-169 (2002).
Cercos-Fortea et al., 16 Biopharmaceutics & Drug Disposition 563-577 (1995).
Merino et al., 10 Biopharmaceutics & Drug Disposition 279-297 (1989).
Moll-Navarro et al., 85(11) Journal of Pharmaceutical Sciences 1248-1254 (1996).
Nacher et al., 15 Biopharmaceutics & Drug Disposition 373-382 (1994).
Schapiro. Current Neurology and Neuroscience Reports 299-302 (2001).
Wuis et al., 12(2) Pharmaceutisch Weekblad Scientific Edition 71-74 (1990).
"Data Sheet: APO Baclofen" http://www.medsafe.govt.nz/profs/datasheet/a/apobaclofentab.htm Jun. 1999.

* cited by examiner

*Primary Examiner* — Nissa Westerberg
(74) *Attorney, Agent, or Firm* — Adriano & Associates

(57) ABSTRACT

The present invention relates generally to pharmaceutical dosage forms comprising: an absorption window active agent; a controlled release component comprising enteric-coated controlled release beads, wherein the enteric-coated release beads comprise at least two pH-sensitive polymer layers. The controlled-release dosage forms provide good bioavailability of absorption window active agents.

45 Claims, 3 Drawing Sheets

PHARMACEUTICAL DOSAGE FORMS HAVING IMMEDIATE RELEASE AND/OR CONTROLLED RELEASE PROPERTIES

CROSS-REFERENCE TO RELATED APPLICATIONS

This Application is a continuation-in-part, and claims the benefit under 35 USC 120 of U.S. patent application Ser. No. 11/138,008, now abandoned filed 26 May 2005; U.S. patent application Ser. No. 10/815,924, now abandoned filed 2 Apr. 2004; U.S. patent application Ser. No. 10/815,926, now abandoned filed 2 Apr. 2004; U.S. patent application Ser. No. 10/815,929, now abandoned filed 2 Apr. 2004; and U.S. patent application Ser. No. 10/815,930, now abandoned filed 2 Apr. 2004; the complete disclosures of which are incorporated herein by reference.

BACKGROUND OF THE INVENTION

The present invention relates to pharmaceutical drug delivery systems for the controlled release of absorption window active agents which: (1) have an absorption window in the gastrointestinal tract (i.e., are usually absorbed in the duodenum and/or jejunum); (2) have a locus of treatment in or proximal to the gastrointestinal tract (e.g., stomach and/or duodenum); or (3) degrade in the colon. The invention also relates to the uses of these controlled release delivery systems in the treatment of various disorders and diseases in mammals.

Conventional drug delivery systems, such as immediate release drug delivery systems, have only limited use for: (1) active agents having an absorption window in the gastrointestinal tract; (2) active agents which have a locus of treatment in or proximal to the gastrointestinal tract; and (3) active agents which degrade in the colon. Conventional sustained release dosage forms of such active agents are difficult to formulate because typical sustained release formulations will release such active agents in areas of the GI tract that do not adequately absorb such active agents. Thus, it is difficult to formulate such active agents in a controlled release formulation to obtain the benefits of the controlled release formulations, such as reducing dosing frequency and minimizing drug plasma level peaks and troughs.

Certain active agents have an absorption window in the gastrointestinal tract. The absorption of these active agents, such as, for example, baclofen, are site specific. Baclofen is primarily absorbed in the upper gastrointestinal (GI) tract. Furthermore, the extent of absorption of baclofen is substantially reduced in the lower GI tract. Absorption may be dose-dependent, being reduced with increasing doses. An improved method of administering an active agent with a limited absorption window, such as baclofen, to a patient would include the delivery of effective amounts of the drug to the upper GI tract for an extended period.

In addition, several side effects may be associated with the administration of active agents to mammals, particularly when administered as immediate release dosage forms. For example, the side effects of baclofen include nausea, vomiting, diarrhea, dizziness, daytime sedation, and less frequently, psychotic states such as depressive mood disorders. In addition, patient compliance with a dosing regimen can be suboptimal where frequent doses are required, such as the need for administering a pharmaceutical dosage form three or four times a day. A pharmaceutical dosage form that requires less frequent dosing, such as once or twice a day, would be preferable. Furthermore, a pharmaceutical dosage form capable of establishing and maintaining stable plasma levels of the active agent for a prolonged period of time may benefit patients by requiring less frequent dosing and/or by minimizing side effects.

Various other formulations for active agents having an absorption window have been described. For example, one pharmaceutical dosage form for baclofen involves adhesive tablets placed in contact with the oral mucosa to deliver the active agent across the mucous membrane. This pharmaceutical dosage form, however, exhibits various known disadvantages associated with adhesive tablets. Furthermore, the adhesive tablets deliver baclofen to a site considered suboptimal for γ-aminobutyric acid (GABA)-related agents. Other proposed formulations for active agents having an absorption window include matrix dosage forms that exhibit marked swelling and high dimensional stability in the swollen state to facilitate extended gastric residence time. In addition, an osmotic pump type dosage form for delivering an active agent with an absorption window has been proposed that provides for the continuous administration of active agent over a prolonged period of time.

Nevertheless, there remains a significant and continuing need for pharmaceutical dosage forms suitable for providing sustained release of active agents having an absorption window. In addition, there remains a need for pharmaceutical dosage forms for active agents with an absorption window that establish and maintain stable plasma levels of the active agent for a prolonged period of time to achieve less frequent dosing and to minimize side effects. These and other objectives are accomplished by the present invention.

BRIEF SUMMARY OF THE INVENTION

The present invention relates generally to pharmaceutical drug delivery systems for the controlled release of absorption window active agents which: (1) have an absorption window in the gastrointestinal tract (e.g., are usually absorbed in the stomach and/or small intestine), (2) have a locus of treatment in or proximal to the gastrointestinal tract (e.g., stomach and/or small intestine); or (3) degrade in the colon. The invention also relates to the uses of these controlled release delivery systems in the treatment of various disorders and diseases in mammals.

It has now been surprisingly found that prolonged duration of absorption window active agents can be achieved with pharmaceutical dosage forms comprising: (i) an absorption window active agent; and (ii) a controlled release component comprising enteric-coated controlled release beads, wherein the enteric-coated release beads comprise at least two pH-sensitive polymer layers. Preferably, the outer pH-sensitive polymer layer dissolves at a lower pH than the inner pH-sensitive polymer layer.

Absorption window active agents suitable for use with the present invention include, but are not limited to: ACE inhibitors, antibiotics, anti-gout agents, anti-hyperlipidemic agents, anti-hypertensive agents, anti-tumor agents, bismuth salts, bronchodilators, COX-2 inhibitors, diuretic agents, GABA receptor agonists, histamine (H2) blockers, nonsteroidal anti-inflammatory agents (NSAIDs), nucleic acid or amino acid derivatives, opioids, peptidomimetic drugs, prostaglandins, therapeutic ions, vitamins, or mixtures of any thereof.

The pharmaceutical dosage forms of the present invention are adapted to provide prolonged in vivo absorption as compared to immediate release active agent formulations.

DETAILED DESCRIPTION OF THE INVENTION

Figure 1:
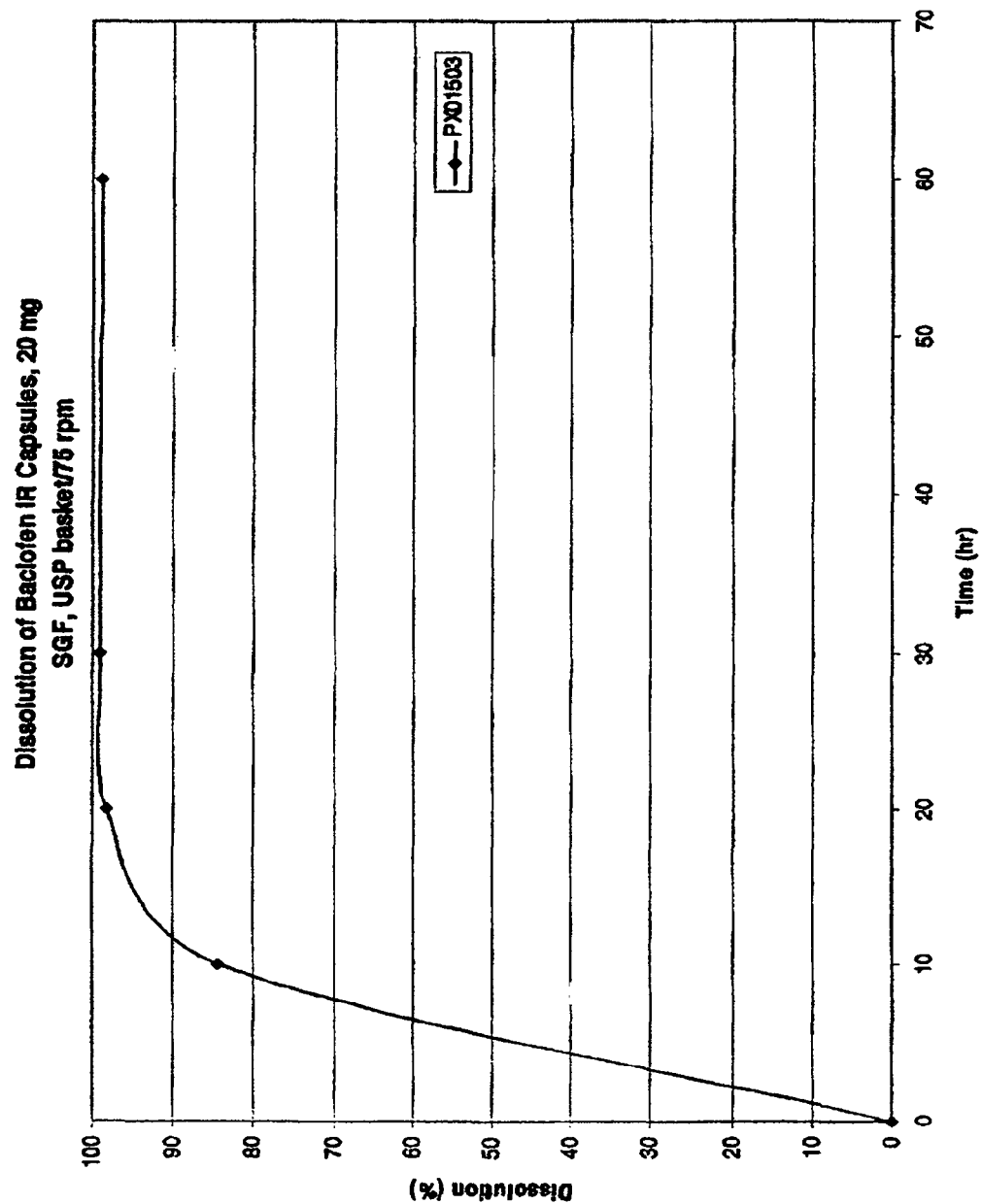
FIG. 1 is a graph of the in vitro dissolution profile of a baclofen capsule formulation, 20 mg, prepared according to Example 2, according to measurements under the USP paddle method of 75 rpm in 900 ml simulated gastric fluid (pH 1.2) at 37° C.

The present invention relates generally to pharmaceutical drug delivery systems for the controlled release of absorption window active agents which: (1) have an absorption window in the gastrointestinal tract (e.g., are usually absorbed in the stomach and/or small intestine); (2) have a locus of treatment in or proximal to the gastrointestinal tract (e.g., stomach and/or small intestine); or (3) degrade in the colon. The invention also relates to the uses of these controlled release delivery systems in the treatment of various disorders and diseases in mammals.

The present invention relates to pharmaceutical dosage forms comprising: (i) an absorption window active agent (which absorption window active agent may include analogs, derivatives, prodrugs, or mixtures thereof, as well as, a racemic mixture of the absorption window active agent or a substantially optically pure isomeric mixture of the absorption window active agent); and (ii) a controlled release component comprising enteric-coated controlled release beads, wherein the enteric-coated release beads comprise at least two pH-sensitive polymer layers.

The enteric-coated controlled release beads of the pharmaceutical dosage form comprise a core of the absorption window active agent, wherein the absorption window active agent is coated with an inner pH-sensitive polymer layer and an outer pH-sensitive polymer layer. According to the present embodiment, the core comprises the absorption window active agent which may be adhered to a sugar sphere. The inner pH-sensitive polymer layer adheres to and substantially envelopes the core. The outer pH-sensitive polymer layer adheres to the inner pH-sensitive polymer layer and substantially envelopes both the core and the inner pH-sensitive polymer layer.

Preferably, the outer pH-sensitive polymer layer dissolves at a lower pH than the inner pH-sensitive polymer layer. The outer pH-sensitive layer delays the release of the absorption window active agent until the pharmaceutical dosage form passes through the stomach and reaches the higher pH environment of the small intestine. At this point the outer pH-sensitive layer will dissolve and expose the inner pH-sensitive layer. The inner pH-sensitive layer, upon exposure to the pH environment of the small intestine, will cause sustained release of the absorption window active agent. The sustained release and/or absorption of the absorption window active agent prior to the passage of the pharmaceutical dosage form beyond the area of the GI tract where the absorption window active agent can be effectively absorbed is controlled by the amount of pH sensitive polymers. In a preferred embodiment, the outer pH-sensitive layer will dissolve at a pH of about 5, about 5.5, about 6, or about 6.5, and the inner pH-sensitive layer will dissolve at a pH of about 5.5, about 6.0, about 6.5, or about 7, respectively.

The dissolution profile of the present invention can be tailored by adjusting the amount of inner pH-sensitive polymer and/or outer pH-sensitive polymer used in the formulation. The amount of inner pH-sensitive polymer and/or outer pH-sensitive polymer can be measured by various means well known in the art, such as, for example, percentage of weight with respect to the enteric-coated controlled release bead, thickness of the coating on the enteric-coated controlled release bead, or percentage of weight with respect to the pharmaceutical dosage form. The outer polymer layer may have a weight percent with respect to the enteric-coated release bead of from about 5% to about 50%, from about 10% to about 40%, or from about 15% to about 35%. The inner polymer layer may have a weight percent with respect to the enteric-coated release bead of from about 5% to about 50%, from about 8% to about 40%, from about 10% to about 35%, or from about 20% to about 30%.

The pharmaceutical dosage form of the present invention may also further comprise an immediate release component. In one embodiment the immediate release component comprises immediate release beads. In this embodiment, the immediate release component exhibits an in vitro dissolution profile in simulated gastric fluid comprising at least about 80% absorption window active agent release after 1 hour.

The immediate release component can comprise any suitable amount of absorption window active agent necessary to produce the desired physiological result. The ratio of the immediate release component to the controlled release component is well known to those of ordinary skill in the art. For example, the ratio of the immediate release component to the controlled release component is from about 1:4 to about 4:1, from about 5:1 to about 1:5, from about 6:1 to about 1:6, from about 7:1 to about 1:7, from about 8:1 to about 1:8, from about 9:1 to about 1:9, from about 1:10 to about 10:1, from about 1:3 to about 3:1, or about 1:1. In another embodiment, the ratio of the immediate release component to the controlled release component is from about 1:2 to about 2:1.

It has been found that the formulations of the present invention may allow for less frequent dosing as compared to immediate release formulations. For example, for patients requiring chronic $GABA_B$ agonist therapy, twice daily administration of the formulations of the present invention is bioequivalent to a three times daily administration of an existing immediate release formulation. This reduced dosing frequency is more convenient for patients and typically leads to better patient compliance. In addition, it reduces the number of plasma peaks and troughs, which is typically associated with improved efficacy and reduced side effects.

Active agents that have an absorption window in the gastrointestinal tract are suitable for use with the pharmaceutical dosage form of the present invention. Examples of such narrow window active agents which are suitable for use with the present invention include, but are not limited to: ACE inhibitors, antibiotics, anti-gout agents, anti-hyperlipidemic agents, anti-hypertensive agents, anti-spasmatic agents, anti-tumor agents, bismuth salts, bronchodilators, COX-2 inhibitors, diuretic agents, GABA receptor agonists, histamine (H2) blockers, nonsteroidal anti-inflammatory agents (NSAIDs), nucleic acid or amino acid derivatives, opioids, peptidomimetic drugs, prostaglandins, therapeutic ions, vitamins, or mixtures of any thereof.

ACE inhibitors suitable for the present invention include, but are not limited to: benazepril, captopril, cilazapril, enalapril, fosinopril, ramipril, or mixtures of any thereof.

Amino acid derivatives suitable for the present invention include, but are not limited to: baclofen, gabapentin, levodopa, α-methyldopa, valacyclovir, or mixtures of any thereof.

Antibiotics suitable for the present invention include, but are not limited to: ciprofloxacin, clarithromycin, metronidazole, nitrofurantoin, tetracycline, β-lactam antibiotics, quinolones, or mixtures of any thereof. β-lactam antibiotics suitable for the present invention include, but are not limited to: amoxicillin, cephalexin, or mixtures thereof. Quinolones suitable for the present invention include, but are not limited to: ciprofloxacin, enoxacin, fleroxacin, lomefloxacin, morfloxacin, ofloxacin, pefloxacin, or mixtures of any thereof.

Anti-hypertensive agents suitable for the present invention include, but are not limited to: atenolol, metoprolol, or mixtures thereof.

As an example, pravastatin is an anti-hyperlipidemic agent suitable for the present invention.

Anti-spasmatic agents suitable for the present invention include, but are not limited to: dantrolene, tizanidine, or mixtures thereof.

Bronchodilators suitable for the present invention include, but are not limited to: albuterol, pirbuterol, or mixtures thereof.

As an example, furosemide is a diuretic agent suitable for the present invention.

Nucleic acid derivatives suitable for the present invention include, but are not limited to: acyclovir, AZT, didanosine, or mixtures of any thereof.

Therapeutic ions suitable for the present invention include, but are not limited to: calcium carbonate, calcium citrate, lithium carbonate, lithium citrate, or mixtures of any thereof.

Vitamins suitable for the present invention include, but are not limited to: ascorbic acid, folic acid, riboflavin, vitamin E, thiamine disulfide, or mixtures of any thereof.

In addition, the pharmaceutical dosage form of the present invention may be used to deliver active agents for local treatment in the gastrointestinal tract. These active agents may be useful for the treatment of, for example, neoplasms of the stomach (e.g., adenocarcinoma of the stomach or gastric lymphoma). Examples of active agents suitable for use with the pharmaceutical dosage form of the present invention and suitable for local treatment in the gastrointestinal tract include, but are no limited to: anti-tumor agents, histamine (H2) blockers, bismuth salts, prostaglandins, nonsteroidal anti-inflammatory agents (NSAIDs), opioids, COX-2 inhibitors, or mixtures of any thereof. These dosage forms can be used in the treatment of various disorders and diseases in mammals.

Anti-tumor agents suitable for the present invention include, but are not limited to: 5-cisplatin, doxorubicin, etoposide, fluorouracil, methotrexate, mitomycin, semustine, or mixtures of any thereof.

Bismuth salts suitable for the present invention include, but are not limited to: bismuth subcitrate, bismuth subsalicylate, or mixtures thereof.

Histamine (H2) blockers suitable for the present invention include, but are not limited to: cimetidine, famotidine, ranitidine, or mixtures of any thereof.

Prostaglandins suitable for the present invention include, but are not limited to: misoprostol, synthetic misoprostol, synthetic prostaglandins, or mixtures of any thereof.

As stated above, the pharmaceutical dosage form of the present invention is also suitable for active agents which may degrade in the colon. An example of an active agent suitable for the present invention because it degrades in the colon is metoprolol.

Additional examples of active agents suitable for the present invention are: allopurinol, chlorpromazine, or mixtures thereof.

The pharmaceutical dosage form of the present invention may exhibit an in vitro dissolution profile in simulated intestinal fluid medium comprising at least about 5% absorption window active agent release after 1 hour, at least about 20% absorption window active agent release after 4 hours, and at least about 30% absorption window active agent release after 6 hours. The pharmaceutical dosage forms of the present invention may also exhibit an in vitro dissolution profile in simulated gastric fluid/simulated intestinal fluid (1 hour switchover) medium comprising from about 2% to about 90% absorption window active agent release after 1 hour, at least about 30% absorption window active agent release after 4 hours, and at least about 40% absorption window active agent release after 6 hours.

Another embodiment of the present invention exhibits an in vivo plasma profile comprising mean maximum absorption window active agent release from about 30 minutes to about 7 hours (preferably from about 1 hour to about 5.5 hours, more preferably from about 90 minutes to about 5.5 hours, and even more preferably from about 2 hours to about 5.5 hours) after administration of a single dose to a fasting patient.

At steady-state, the pharmaceutical dosage forms of the present invention will reach a $C_{MIN}$ comparable to that obtained at steady-state from an immediate-release dosage form at a later time point, which will allow less frequent dosing. In particular, a pharmaceutical dosage form of the present invention, when administered twice daily, will deliver mean steady-state area under the plasma concentration-time curve (AUC), maximum plasma concentration ($C_{MAX}$), and minimum plasma concentration ($C_{MIN}$) similar to that of an immediate-release tablet formulation administered three times daily.

In an alternate embodiment, the pharmaceutical dosage form of the present invention exhibits an in vivo plasma profile comprising at least 2 hours of sustained absorption window active agent concentrations at greater than therapeutic levels, after about 2 hours following administration to a fasting patient.

The pharmaceutical dosage forms of the present invention contain a controlled release component, where a controlled release component comprises enteric-coated release beads comprise at least two pH-sensitive polymer layers. The enteric-coated release beads may also comprise the absorption window active agent. The controlled release component exhibits an in vitro dissolution profile in simulated gastric fluid/simulated intestinal fluid (2 hour switchover) medium comprising less than about 10% absorption window active agent release after 2 hours, at least about 40% absorption window active agent release after 3 hours, and at least about 70% absorption window active agent release after 6 hours. Preferably, the controlled release component exhibits an in vitro dissolution profile in simulated gastric fluid/simulated intestinal fluid (2 hour switchover) medium comprising less than about 10% absorption window active agent release after 2 hours, at least about 50% absorption window active agent release after 3 hours, and at least about 80% absorption window active agent release after 6 hours. Most preferably, the controlled release component exhibits an in vitro dissolution profile in simulated gastric fluid/simulated intestinal fluid (2 hour switchover) medium comprising less than about 10% absorption window active agent release after 2 hours, at least about 60% absorption window active agent release after 3 hours, and at least about 90% absorption window active agent release after 6 hours.

The present invention includes pharmaceutical dosage forms having both immediate release and controlled release components. In this embodiment, the pharmaceutical dosage form exhibits an in vitro dissolution profile in simulated gastric fluid/simulated intestinal fluid (2 hour switchover) medium comprising less than about 75% absorption window active agent release after 2 hours, and at least about 80% absorption window active agent release after 3 hours. Preferably, the pharmaceutical dosage form exhibits an in vitro dissolution profile in simulated gastric fluid/simulated intestinal fluid (2 hour switchover) medium comprising less than about 65% absorption window active agent release after 2 hours, and at least about 90% absorption window active agent release after 3 hours Appropriate in vitro dissolution testing methods for the dosage forms of the present invention are known to those of skill in the art and include those described in the Examples herein. The USP paddle method refers to the Paddle and Basket Method as described in United States Pharmacopoeia, Edition XXII (1990). In particular, the USP paddle method of 50 rpm or 75 rpm in 900 ml simulated gastric fluid (SGF) (pH 1.2) or simulated intestinal fluid (SIF) (pH 6.8) at 37° C. may be used to determine the in vitro dissolution profiles according to the present invention.

The pharmaceutical dosage forms of the present invention are adapted to allow prolonged absorption of the absorption window active agent, which allows for less frequent administration as compared to existing immediate-release formulations. As used herein, "prolonged absorption" means that the absorption window active agent is absorbed in vivo, under fasting conditions, over an extended period of time. In a preferred embodiment comprising both an immediate release component and a controlled release component, the time period over which the majority (i.e., 80-90%) of the absorption occurs extends to about 7 or 8 hours after administration of the dosage form. Specifically, the median time period at which at least 80% of the absorption window active agent is absorbed from the dosage forms of the present invention is greater than 2.5 hours after administration, typically three to 4.5 hours after administration. By comparison, the median time period at which at least 80% of the absorption window active agent is absorbed from existing immediate-release formulations is 1.5 to two hours after administration. The period over which an absorption window active agent is absorbed from a dosage form can be calculated by deconvolution using mathematical methods known to those of skill in the art.

Total daily dosages of the compounds useful according to this invention administered to a host in single or divided doses are generally in amounts of from about 0.01 mg/kg to about 100 mg/kg body weight daily, preferably from about 0.05 mg/kg to about 50 mg/kg body weight daily, from about 0.1 mg/kg to about 45 mg/kg body weight daily, from about 0.15 mg/kg to about 40 mg/kg body weight daily, from about 0.2 mg/kg to about 35 mg/kg body weight daily, or from about 0.2 mg/kg to about 30 mg/kg body weight daily. It should be understood, however, that the specific dose level for any particular patient will depend upon a variety of factors including body weight, general health, gender, diet, time and route of administration, rates of absorption and excretion, combination with other drugs, and the severity of the particular disease being treated. Actual dosage levels of the absorption window active agent in the compositions of the present invention may be varied so as to obtain an amount of absorption window active agent that is effective to obtain a desired therapeutic response for a particular composition and method of administration.

Total daily dose of the active agents useful according to this invention that are administered to a host in single or divided doses may be in amounts, for example, of from about 0.01 mg/kg to about 20 mg/kg body weight daily, and preferably 0.02 to 10 mg/kg/day, from about 0.03 mg/kg to about 15 mg/kg body weight daily, from about 0.05 mg/kg to about 10 mg/kg body weight daily, or from about 0.1 mg/kg to about 5 mg/kg body weight daily. The preferred dosage range of the absorption window active agent is between 2.5 mg and 100 mg per dosage form. Dosage forms according to the present invention may contain such amounts or fractions thereof as may be used to make up the daily dose.

The pharmaceutical dosage form of the present invention (preferably a tablet or capsule, which may contain beads, granules, particles, or a mixture thereof) may contain an absorption window active agent in an amount of from about 1 mg to about 1000 mg, from about 1.5 mg to about 500 mg, from about 2 mg to about 250 mg, from about 2.5 mg to about 200 mg, from about 3 mg to about 175 mg, from about 3.5 mg to about 150 mg, from about 4 mg to about 125 mg, from about 10 mg to about 100 mg, from about 12 mg to about 75 mg, from about 15 mg to about 50 mg, from about 17 mg to about 45 mg, from about 20 mg to about 40 mg, from about 25 mg to about 35 mg, and can be used in the treatment of various disorders and diseases in mammals. In addition, the pharmaceutical dosage form of the present invention may contain an absorption window active agent in an amount of from about 200 mg to about 1000 mg, from about 300 mg to about 900 mg, from about 400 mg to about 800 mg, from about 450 mg to about 750 mg, from about 500 mg to about 700 mg, from about 550 mg to about 650 mg.

Typically, the optimal dosage for a patient will be determined by titration, whereby the patient is initially given small doses, which are then gradually increased until the patient reaches the dosage level that achieves maximum therapeutic efficacy with minimum side effects.

Among pharmaceutical dosage forms apparent to the skilled artisan, the solid oral dosage form according to the present invention may be a tablet formulation, or a discrete unit-filled capsule formulation, or a sachet formulation. The discrete units of the present invention include beads, granules, pellets, spheroids, particles, tablets, pills, etc.

Dosage forms can be made according to known methods in the art. Some preferred methods are described below.

Particle Based Dosage Forms, Immediate Release Particles. The immediate release/controlled release dosage forms of the present invention can also take the form of pharmaceutical particles. The pharmaceutical dosage forms can include immediate release particles in combination with controlled release particles in a ratio sufficient to deliver the desired release of absorption window active agents. The controlled release particles can be produced by coating the immediate release particles.

The term "particle" as used herein means a granule having a diameter of between about 0.01 mm and about 5.0 mm, preferably between about 0.1 mm and about 2.5 mm, and more preferably between about 0.5 mm and about 2 mm. The skilled artisan should appreciate that particles according to the present invention can be any geometrical shape within this size range. So long as the mean for a statistical distribution of particles falls within the particle sizes enumerated above, they will be considered to fall within the contemplated scope of the present invention. Particles can assume any standard structure known in the pharmaceutical arts. Such structures include, for example, matrix particles, non-pareil cores having a drug layer and active or inactive cores having multiple layers thereon. A controlled release coating can be added to any of these structures to create a controlled release particle.

The particles can be produced according to any of a number of known methods for making particles. The immediate release particles comprise the absorption window active agent and a disintegrant. Suitable disintegrants include, for example, starch, low-substitution hydroxypropyl cellulose, croscarmellose sodium, calcium carboxymethyl cellulose, hydroxypropyl starch, sodium starch glycolate, and microcrystalline cellulose.

In addition to the above-mentioned ingredients, the pharmaceutical dosage form may also contain suitable quantities of other materials, for example, diluents, lubricants, binders, granulating aids, colorants, flavorants, and glidants that are conventional in the pharmaceutical arts. The quantities of these additional materials are sufficient to provide the desired effect to the desired formulation. A pharmaceutical dosage form incorporating particles may also contain suitable quantities of these other materials such as diluents, lubricants, binders, granulating aids, colorants, flavorants, and glidants that are conventional in the pharmaceutical arts in amounts of up to about 75% by weight of the particulate, if desired.

In one preferred embodiment, oral dosage forms are prepared to include an effective amount of particles as described above within a capsule. For example, melt-extruded particles may be placed in a gelatin capsule in an amount sufficient to provide an effective controlled release dose when ingested and contacted by gastric fluid. In another preferred embodiment, a suitable amount of the particles are compressed into an oral tablet using conventional tableting equipment using standard techniques. Techniques and compositions for making tablets (compressed and molded), capsules (hard and soft gelatin), and pills are also described in REMINGTON'S PHARMACEUTICAL SCIENCES, Arthur Osol, ed., 1553-93 (1980), incorporated herein by reference. The particles can be made by mixing the relevant ingredients and granulating the mixture. The resulting particles are dried and screened, and the particles having the desired size are used for drug formulation.

Enteric Coated Controlled Release. The controlled release of the absorption window active agent is achieved with coatings of at least two pH-sensitive polymers. The outer pH-sensitive polymer functions as a delayed or delayed-sustained release enteric coating. Any commercially available pH-sensitive polymers may be used for each of the two pH-sensitive coatings. The absorption window active agent is minimally or not released in the acidic stomach environment of pH of about 4.5 or less. The absorption window active agent should become available when the enteric layer dissolves at the higher pH present in the intestine; after a suitable delayed time; or after the unit passes through the stomach. The preferred duration of drug release time is in the range of up to about 7 hours after dosing under fasting conditions.

Enteric polymers include cellulose acetate phthalate, cellulose acetate trimellitate, hydroxypropyl methylcellulose phthalate, polyvinyl acetate phthalate, carboxymethylethylcellulose, co-polymerized methacrylic acid/methacrylic acid methyl esters such as, for instance, materials known under the trade name Eudragit® L12.5, Eudragit® L100, or Eudragit® S12.5, S100 (Röhm GmbH, Darmstadt, Germany) or similar compounds used to obtain enteric coatings. Aqueous colloidal polymer dispersions or re-dispersions can be also applied, e.g., Eudragit® L 30D-55, Eudragit® L100-55, Eudragit® S100, Eudragit® preparation 4110D c; Aquateric®, Aquacoat® CPD 30 (FMC Corp.); Kollicoat MAE® 30D and Kollicoat MAE® 30DP (BASF); Eastacryl® 30D (Eastman Chemical, Kingsport, Tenn.).

The enteric polymers used in this invention can be modified by mixing with other known coating products that are not pH sensitive. Examples of such coating products include the neutral methacrylic acid esters with a small portion of trimethylammonioethyl methacrylate chloride, sold currently under the trade names E Eudragit®, Eudragit® RL, Eudragit® RS; a neutral ester dispersion without any functional groups, sold under the trade names Eudragit® NE30D and Eudragit® NE30; and other pH independent coating products.

The enteric coating will substantially envelop the controlled-release component. The term "substantially envelop" is intended to define the total or near-total enclosure of a component. Such an enclosure includes, preferably, at least about 80% enclosure, more preferably at least about 90% enclosure, and even more preferably at least about 99% enclosure.

In a preferred embodiment, the dosage form is a capsule formulation, which capsule contains a combination of beads containing the absorption window active agent in an immediate-release formulation and beads containing the absorption window active agent in an enteric-coated controlled-release formulation. In this preferred embodiment, the enteric-coated controlled-release beads contain two pH-sensitive layers that control the rate of absorption window active agent release.

The controlled-release beads are prepared by coating the absorption window active agent on sugar spheres, then coating the inner pH-sensitive polymer onto the absorption window active agent coated sugar spheres, followed by coating the outer pH-sensitive polymer onto the sugar spheres coated with the absorption window active agent and the inner pH-sensitive polymer. Preferably, the outer pH-sensitive polymer layer will dissolve at a pH of about 5.5 or greater. In an alternate embodiment, the outer pH-sensitive polymer layer will dissolve at a pH of about 3 or higher, at a pH of about 3.5 or higher, at a pH of about 4 or higher, at a pH of about 4.5 or higher, at a pH of about 5 or higher, at a pH of about 5.5 or higher, at a pH of about 6 or higher, or at a pH of about 6.5 or higher.

The inner pH-sensitive layer functions to provide sustained release of the absorption window active agent upon dissolution of the outer enteric coat.

The inner pH-sensitive polymer layer will be applied in an amount such that, in combination with the outer pH-sensitive polymer layer, the enteric-coated controlled release component yields improved bioavailability of the absorption window active agent. Preferably, the inner pH-sensitive polymer layer will dissolve at pH of about 6 or higher. In an alternate embodiment, the inner pH-sensitive polymer layer will dissolve at a pH of about 4 or higher, at a pH of about 4.5 or higher, at a pH of about 5 or higher, at a pH of about 5.5 or higher, at a pH of about 6.5 or higher, or at a pH of about 7 or higher. Particularly preferred polymers are described in the Examples that follow.

An embodiment of the present invention provides for a free flowing formulation comprising the absorption window active agent. The term "free flowing" as used herein, means dosage forms that pass through a patient's digestive system without impediment or mechanism to slow passage. Thus, for example, the term "free flowing" would exclude gastric raft type dosage forms, which are designed to reside in the stomach for extended periods as in, e.g., U.S. Pat. No. 5,651,985.

Dosage forms according to the present invention can also include a combination of the absorption window active agent and at least one additional active agent, such as tizanidine, dantrolene, nonsteroidal anti-inflammatory agents (NSAIDs), opioids, and COX-2 inhibitors. The other active agents can be co-formulated in the immediate-release or controlled-release components to provide desirable therapeutic effects.

Dosage levels of the absorption window active agent, as well as any active agent that is to be used in combination with the absorption window active agent, in the compositions may be varied so as to obtain an amount of the absorption window active agent, and, when used as a combination product, an amount of active ingredient that is effective to obtain a desired therapeutic response for a particular composition and method of administration.

An object of the present invention provides for controlled bioavailability of the absorption window active agent as desired by health providers. Bioavailability refers to the degree to which the therapeutically active medicament becomes available in the body after administration. Typically, bioavailability is measured in patients who fasted overnight before being dosed with the test preparation. Plasma samples are then taken and analyzed for the plasma concentration of the parent compound and/or its active metabolite. These data may be expressed as $C_{MAX}$, the maximum amount of active ingredient found in the plasma, or as AUC, the area under the plasma concentration time curve. Shargel & Yu, APPLIED BIOPHARMACEUTICS AND PHARMACOKINETICS ch. 10 (3d ed. 1996); see also APPLIED PHARMACOKINETICS: PRINCIPLES OF THERAPEUTIC DRUG MONITORING, Evans et al., eds. (3d ed. 1992).

For example, the absorption window active agent formulations may be used in a comparative bioavailability study in subjects. Subjects fast over night prior to drug administration. Plasma samples are then taken at dosing, and every hour for twelve hours after dosing, and then at sixteen and twenty-four hours after dosing, and analyzed for the ng/ml concentration of absorption window active agent or metabolites thereof.

As used herein, the term "absorption window active agent" refers to those active agents which are absorbed in a particular location of the gastrointestinal tract, would benefit the patient by being absorbed in a particular location of the gastrointestinal tract, or would degrade in a different location of the gastrointestinal tract. Absorption window active agents differ from active agents which have no window of absorption and, thus, are absorbed throughout the entire GI tract. The absorption window could be due to any number of reasons, for example, physiological characteristics of the GI tract, location of active transport mechanisms along the GI tract, or the pharmacological and/or absorption characteristics of the active agent. For example, certain active agents, such as baclofen, are more readily absorbed in the upper portion of the small intestine and are not well absorbed in the large intestine. In a preferred embodiment, the absorption window active agent is more readily absorbed in the stomach and/or small intestine. In another embodiment, the absorption window active agent is more readily absorbed in the stomach. In an alternative embodiment, the absorption window active agent is more readily absorbed in the small intestine. More preferably, the absorption window active agent is more readily absorbed in the upper small intestine. In yet another embodiment, the absorption window active agent is more readily absorbed in the duodenum. Alternatively, the absorption window active agent is more readily absorbed in the jejunum. Moreover, the absorption window active agent is absorbed in the ileum.

Any active agent having a therapeutic effect in the gastrointestinal tract, or that has an absorption window in the gastrointestinal tract, or that should be administered at a particular location in the GI tract, or that degrades in the colon, other than the aforementioned agents, may be delivered by the pharmaceutical dosage form of the present invention. Such active agents are well known to persons having ordinary skill in the art and may be delivered alone or in combination with other suitable active agents.

The term "analog" means a compound which comprises a chemically modified form of a specific compound or class thereof, and which maintains the pharmaceutical and/or pharmacological activities characteristic of said compound or class.

The term "derivative" means a chemically modified compound wherein the modification is considered routine by the ordinary skilled chemist, such as an ester or an amide of an acid, protecting groups, such as a benzyl group for an alcohol or thiol, and tert-butoxycarbonyl group for an amine.

The term "prodrug", as used herein, includes any covalently bonded carriers which release an active parent drug of the present invention in vivo when such prodrug is administered to a patient. Because prodrugs are known to enhance numerous desirable qualities of pharmaceuticals (i.e., solubility, bioavailability, manufacturing, etc.) the compounds of the present invention may be delivered in prodrug form. Prodrugs of the present invention may be prepared by modifying functional groups present in the compound in such a way that the modifications are cleaved, either in routine manipulation or in vivo, to the parent compound. The transformation in vivo may be, for example, as the result of some metabolic process, such as chemical or enzymatic hydrolysis of a carboxylic, phosphoric or sulphate ester, or reduction or oxidation of a susceptible functionality. Prodrugs within the scope of the present invention include compounds wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Functional groups that may be rapidly transformed, by metabolic cleavage, in vivo form a class of groups reactive with the carboxyl group of the compounds of this invention. They include, but are not limited to, such groups as alkanoyl (such as acetyl, propionyl, butyryl, and the like), unsubstituted and substituted aroyl (such as benzoyl and substituted benzoyl), alkoxycarbonyl (such as ethoxycarbonyl), trialkysilyl (such as trimethyl- and triethysilyl), monoesters formed with dicarboxylic acids (such as succinyl), and the like. Because of the ease with which metabolically cleavable groups of the compounds useful according to this invention are cleaved in vivo, the compounds bearing such groups act as prodrugs. The compounds bearing the metabolically cleavable groups have the advantage that they may exhibit improved bioavailability as a result of enhanced solubility and/or rate of absorption conferred upon the parent compound by virtue of the presence of the metabolically cleavable group.

A discussion of prodrugs is provided in the following: DESIGN OF PRODRUGS, H. Bundgaard, ed. (Elsevier, 1985); METHODS IN ENZYMOLOGY, K. Widder et al., eds., vol. 42, 309-96 (Academic Press 1985); A TEXTBOOK OF DRUG DESIGN AND DEVELOPMENT, Krogsgaard-Larsen & H. Bundgaard, ed., Chapter 5; *Design and Applications of Prodrugs,* 113-91 (1991); H. Bundgard, *Advanced Drug Delivery Reviews,* 1-38 (1992); 8 J. PHARM. SCIENCES 285 (1988); N. Nakeya et al., 32 CHEM. PHARM. BULL. 692 (1984); T. Higuchi and V. Stella, *Prodrugs as Novel Delivery Systems,* 14 A.C.S. SYMPOSIUM SERIES: BIOREVERSIBLE CARRIERS IN DRUG DESIGN, Edward B. Roche, ed. (Am. Pharm. Assoc. & Pergamon Press 1987), each of which is incorporated herein by reference.

The term "metabolite" refers to a form of a compound obtained in a human or animal body by action of the body on the administered form of the compound, for example a de-methylated analog of a compound bearing a methyl group which is obtained in the body after administration of the methylated compound as a result of action by the body on the methylated compound. Metabolites may themselves have biological activity.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

For example, "pharmaceutically acceptable salts" refer to derivatives of the disclosed compounds wherein the specified compound is converted to an acid or base salt thereof. Such pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluensulfonic, methanesulfonic, ethane dislfonic, oxalic, isethionic, and the like.

For purposes of the present invention, the term "controlled release" refers to part or all of a dosage form that can release one or more active pharmaceutical agents over a prolonged period of time (i.e., over a period of more than 1 hour), or delays the release of active agent for a prolonged period of time. The characteristic of controlled release (CR) may also be referred to as sustained release (SR), prolonged release (PR), modified release (MR), delayed release (DR) or extended release (ER). When used in association with the dissolution profiles discussed herein, the term "controlled release" refers to that portion of a dosage form according to the present invention that delivers active agent over a period of time greater than 1 hour.

"Immediate release" refers to part or all of a dosage form that releases active agent substantially immediately upon contact with gastric juices and that results in substantially complete dissolution within about 1 hour. The characteristic of immediate release (IR) may also be referred to as instant release (IR). When used in association with the dissolution profiles discussed herein, the term "immediate release" refers to that portion of a dosage form according to the present invention that delivers active agent over a period of time less than 1 hour.

The term "$C_{MAX}$" is the peak blood plasma concentration exhibited by the compositions of the present invention. "$T_{MAX}$" refers to the time that $C_{MAX}$ occurs in the plasma concentration-time profile. "$C_{MIN}$" is the minimum plasma concentration. "C" is shorthand for concentration, "T" for time, "max" for maximum, and "min" for minimum. Initial peak plasma level refers to the first rise in blood plasma level of the active agent and may be followed by one or more additional peaks, one of which may be $C_{MAX}$. As used herein, "mean maximum absorption window active agent level" refers to the mean absorption window active agent $C_{MAX}$. The blood plasma concentrations described herein are typically determined across a population of at least 12 subjects.

The blood plasma concentrations described above may refer to plasma levels after a single oral administration of the dosage form, or may refer to levels obtained at steady state. As used herein, "steady state" blood plasma concentrations refers to the plasma levels obtained upon the repeated dosing of a drug until it reaches a stable level of absorption and elimination such that the amount of drug in the body is substantially constant.

As used herein, the term "patient" means any mammal including humans.

The term "effective amount" means an amount of a compound/composition according to the present invention effective in producing the desired therapeutic effect.

The term "excipients" refer to pharmacologically inert ingredients that are not active in the body. See HANDBOOK OF PHARMACEUTICAL EXCIPIENTS (Am. Pharm. Ass'n 1986). A person of ordinary skill in the art will recognize that many different excipients can be used in formulations according to the present invention and the list provided herein is not exhaustive.

The active agents of the present invention may be mixed with pharmaceutically acceptable carriers, diluents, adjuvants, excipients, or vehicles, such as preserving agents, fillers, polymers, disintegrating agents, glidants, wetting agents, emulsifying agents, suspending agents, sweetening agents, flavoring agents, perfuming agents, lubricating agents, acidifying agents, and dispensing agents, depending on the nature of the mode of administration and dosage forms. Such ingredients, including pharmaceutically acceptable carriers and excipients, may be used to formulate oral dosage forms. Pharmaceutically acceptable carriers include water, ethanol, polyols, vegetable oils, fats, waxes polymers, including gel forming and non-gel forming polymers, and suitable mixtures thereof. Examples of excipients include starch, pregelatinized starch, Avicel, lactose, milk sugar, sodium citrate, calcium carbonate, dicalcium phosphate, and lake blend. Examples of disintegrating agents include starch, alginic acids, and certain complex silicates. Examples of lubricants include magnesium stearate, sodium lauryl sulphate, talc, as well as high molecular weight polyethylene glycols.

"Dosing under fasting conditions" is defined as when the dosage is administered orally with 240 ml of room temperature water after subjects are fasted overnight for at least 10 hours. No fluid, except that given with drug administration, will be allowed from 1 hour prior to dose administration until 1 hour after dosing. At 2 hours post-dose, subjects may consume 240 ml of room temperature water.

As used herein and in the claims, the singular forms "a," "an," and "the" include the plural reference unless the context clearly indicates otherwise. Thus, for example, the reference to a profile is a reference to one or more such profiles, including equivalents thereof known to those skilled in the art. Other than in the operating examples, or where otherwise indicated, all numbers expressing quantities of ingredients or reaction conditions used herein should be understood as modified in all instances by the term "about."

All patents and other publications identified are incorporated herein by reference for the purpose of describing and disclosing, for example, the methodologies described in such publications that might be used in connection with the present invention.

Unless defined otherwise, all technical and scientific terms used herein have the same meaning as those commonly understood to one of ordinary skill in the art to which this invention pertains. Although any known methods, devices, and materials may be used in the practice or testing of the invention, the preferred methods, devices, and materials in this regard are described herein.

Without further elaboration, one skilled in the art having the benefit of the preceding description can utilize the present invention to the fullest extent. The following examples are illustrative only and do not limit the remainder of the disclosure in any way.

EXAMPLES

Example 1

Active Baclofen-coated Seeds

| FORMULATION | | |
|---|---|---|
| INGREDIENT | % | Mg |
| Sugar Spheres, NF (mesh 20-25) | 81.4 | 250.0 |
| Micronized Baclofen, USP | 13.0 | 40.0 |
| Povidone, USP (Plasdone K-29/32) | 5.6 | 17.14 |
| Purified Water, USP | N/A | N/A |
| TOTAL: | 100.0 | 307.14 |

Povidone (Plasdone K-29/32®) is added to purified water and mixed until the povidone is fully dissolved. Baclofen is mixed in the above solution until uniformly dispersed. A fluidized bed coating apparatus is then used to coat the sugar spheres with the baclofen suspension to produce active coated seeds.

Example 2

Active Baclofen-coated Seeds

| FORMULATION | | |
|---|---|---|
| INGREDIENT | % | Mg |
| Sugar Spheres, NF (mesh 20-25) | 81.4 | 250.0 |
| Micronized Baclofen, USP | 13.0 | 40.0 |
| Hypromellose, Type 2910, USP (Pharmacoat 606, 6 cps) | 5.6 | 17.14 |
| Purified Water, USP | N/A | N/A |
| TOTAL: | 100.0 | 307.14 |

Hypromellose, Type 2910®, USP (Pharmacoat 606, 6 cps) is added to a suitable amount of purified water and mixed until the Hypromellose is fully dissolved. Baclofen is mixed in the above solution until uniformly dispersed. A fluidized bed coating apparatus is then used to coat the sugar spheres with the baclofen suspension to produce active coated seeds.

The dissolution profile of this formulation is shown in FIG. 1.

Example 3

Active Baclofen-containing Granules

| FORMULATION | | |
|---|---|---|
| INGREDIENT | % | Mg |
| Baclofen, USP | 7.4 | 20.0 |
| Pregelatinized Starch, NF (Starch 1500) | 21.3 | 57.5 |
| Microcrystalline Cellulose, NF (Avicel PH-102) | 70.8 | 191.3 |
| Magnesium Stearate, NF | 0.5 | 1.3 |
| Purified Water, USP | N/A | N/A |
| TOTAL: | 100.0 | 270.1 |

Mix Baclofen, Starch 1500 (pregelatinized starch) and Avicel PH-102 (microcrystalline cellulose). Charge the baclofen mixture into a Hobart mixer and blend to form a uniform mixture. Granulate the mixture with purified water to form a granulate. Dry the granulate in an oven at a temperature of 60° C. to form granules. Screen the granules using a #30 mesh screen. Mix magnesium stearate to form active granules.

Example 4

Composition Containing Baclofen Active Coated and Enteric-coated Seeds

| | Formulation | | | | | |
|---|---|---|---|---|---|---|
| | IR Per Capsule | | EC Per Capsule | | Total Per Capsule | |
| Ingredient | % (w/w) | Amount (mg) | % (w/w) | Amount (mg) | % (w/w) | Amount (mg) |
| Micronized Baclofen | 13.36 | 19.00 | 21.87 | 21.00 | 16.79 | 40.00 |
| Sugar Spheres, NF (Mesh 20-25) | 83.48 | 118.73 | 34.11 | 32.75 | 63.58 | 151.48 |
| Hypromellose, Type 2910, USP (Pharmacoat 606, 6 cps) | 2.67 | 3.80 | 4.37 | 4.20 | 3.36 | 8.00 |
| Talc, USP (ALTALC 500 V USP BC (*1814)) | 0.49 | 0.70 | 9.60 | 9.22 | 4.16 | 9.92 |
| Methacrylic Acid Copolymer, Type C, NF (Eudragit L100-55) | — | — | 15.53 | 14.91 | 6.26 | 14.91 |
| Methacrylic Acid Copolymer, Type A, NF (Eudragit L100) | — | — | 10.61 | 10.19 | 4.28 | 10.19 |
| Triethyl Citrate NF | — | — | 3.91 | 3.75 | 1.57 | 3.75 |
| Total | 100.0 | 142.23 | 100.00 | 96.02 | 100.00 | 238.25 |

Hypromellose, Type 2910, USP is added to a suitable amount of purified water and mixed until the hypromellose is fully dissolved. Baclofen is then mixed in the above solution until uniformly dispersed. The suspension is passed through a #40 mesh sieve into a stainless steel container. Sugar spheres are charged into a fluid-bed coater equipped with a Wurster insert and heated until exhaust air temperature reaches 50±5° C. The active suspension from above is sprayed to coat the sugar spheres, which are then dried at a temperature of 60±10° C. for 5-30 minutes. The IR seeds are passed through a #16 mesh stainless steel screen. Acceptable IR seeds are collected and mixed with talc, USP in a slant cone blender for one to ten minutes.

An enteric solution is prepared by mixing isopropyl alcohol and acetone. Triethyl citrate and methacrylic acid copolymer, type A, are stirred into the mixture until completely dissolved. Talc is mixed in the above solution until completely dispersed. A fluidized bed coating apparatus is then used to coat IR seeds prepared as above with the enteric solution to produce enteric-coated seeds. The enteric-coated seeds are passed through a #14 mesh stainless steel screen. Acceptable enteric-coated seeds are collected for second layer enteric-coating.

A second enteric solution is prepared by mixing purified water and acetone. Triethyl citrate and methacrylic acid copolymer, type C, are stirred into the mixture until completely dissolved. Talc is mixed in the above solution until completely dispersed. A fluidized bed coating apparatus is then used to coat enteric-coated seeds prepared as above with the enteric solution to produce the enteric-coated seeds. The enteric-coated seeds are passed through a #12 mesh stainless steel screen. Acceptable enteric-coated seeds are collected and mixed with talc, USP in a slant cone blender for one to ten minutes.

An appropriate amount of IR seeds plus the appropriate amount of enteric-coated seeds are encapsulated to yield Baclofen ER capsules.

Example 5

Baclofen ER Capsules

Baclofen ER capsules having the following formulations were prepared according to the process described in Example 4.

| | Composition of Baclofen ER (ER2A) Capsules 30 mg (Lot PB02003) IR/ER (EC2) = 2:1 | | | | | |
|---|---|---|---|---|---|---|
| | IR Per Capsule | | EC2 Per Capsule | | Total Per Capsule | |
| Ingredient | % (w/w) | Amount (mg) | % (w/w) | Amount (mg) | % (w/w) | Amount (mg) |
| Micronized Baclofen | 8.34 | 20.0 | 4.17 | 10.0 | 12.51 | 30.0 |
| Sugar Spheres, NF (Mesh 20-25) | 52.14 | 125.0 | 26.07 | 62.5 | 78.21 | 187.5 |
| Hypromellose, Type 2910, USP (Pharmacoat 606, 6 cps) | 1.67 | 4.0 | 0.83 | 2.0 | 2.50 | 6.0 |
| Talc, USP (ALTALC 500 V USP BC (*1814)) | 0.33 | 0.8 | 1.38 | 3.29 | 1.71 | 4.09 |
| Methacrylic Acid Copolymer, Type C, NF (Eudragit L100-55) | — | — | 1.68 | 4.03 | 1.68 | 4.03 |
| Methacrylic Acid Copolymer, Type A, NF (Eudragit L100) | — | — | 2.76 | 6.62 | 2.76 | 6.62 |
| Triethyl Citrate NF | — | — | 0.63 | 1.5 | 0.63 | 1.5 |
| Total | 62.48 | 149.8 | 37.52 | 89.94 | 100.00 | 239.74 |

| | Composition of Baclofen ER (ER2B) Capsules 30 mg (Lot PB02103) IR/ER (EC2) = 1:2 | | | | | |
|---|---|---|---|---|---|---|
| | IR Per Capsule | | EC2 Per Capsule | | Total Per Capsule | |
| Ingredient | % (w/w) | Amount (mg) | % (w/w) | Amount (mg) | % (w/w) | Amount (mg) |
| Micronized Baclofen | 3.92 | 10 | 7.85 | 20.0 | 11.78 | 30.0 |
| Sugar Spheres, NF (Mesh 20-25) | 24.53 | 62.5 | 49.06 | 125.0 | 73.59 | 187.5 |
| Hypromellose, Type 2910, USP (Pharmacoat 606, 6 cps) | 0.78 | 2.0 | 1.57 | 4.0 | 2.35 | 6.0 |
| Talc, USP (ALTALC 500 V USP BC (*1814)) | 0.16 | 0.4 | 2.58 | 6.58 | 2.74 | 6.98 |
| Methacrylic Acid Copolymer, Type C, NF (Eudragit L100-55) | — | — | 3.16 | 8.06 | 3.16 | 8.06 |
| Methacrylic Acid Copolymer, Type A, NF (Eudragit L100) | — | — | 5.20 | 13.24 | 5.20 | 13.24 |
| Triethyl Citrate NF | — | — | 1.18 | 3.0 | 1.18 | 3.0 |
| Total | 29.39 | 74.9 | 70.60 | 179.88 | 100.00 | 254.78 |

Example 6

Baclofen ER Capsules

Baclofen ER capsules having the following composition were prepared according to the method described in Example 10. Capsules were prepared having 10 mg, 15 mg, 20 mg, 25 mg, 30 mg, 35 mg and 40 mg baclofen, with the different dosage strengths being directly proportional.

Composition of Baclofen ER Capsules 40 mg (Lot RB04042-60A) IR/EC = 19:21

| Ingredient | IR Per Capsule % (w/w) | IR Per Capsule Amount (mg) | EC Per Capsule % (w/w) | EC Per Capsule Amount (mg) | Total Per Capsule % (w/w) | Total Per Capsule Amount (mg) |
|---|---|---|---|---|---|---|
| Micronized Baclofen | 13.36 | 19.00 | 21.87 | 21.00 | 16.79 | 40.00 |
| Sugar Spheres, NF (Mesh 20-25) | 83.48 | 118.73 | 34.11 | 32.75 | 63.58 | 151.48 |
| Hypromellose, Type 2910, USP (Pharmacoat 606, 6 cps) | 2.67 | 3.80 | 4.37 | 4.20 | 3.36 | 8.00 |
| Talc, USP (ALTALC 500 V USP BC (*1814)) | 0.49 | 0.70 | 9.60 | 9.22 | 4.16 | 9.92 |
| Methacrylic Acid Copolymer, Type C, NF (Eudragit L100-55) | — | — | 15.53 | 14.91 | 6.26 | 14.91 |
| Methacrylic Acid Copolymer, Type A, NF (Eudragit L100-55) | — | — | 10.61 | 10.19 | 4.28 | 10.19 |
| Triethyl Citrate NF | — | — | 3.91 | 3.75 | 1.57 | 3.75 |
| Total | 100.0 | 142.23 | 100.00 | 96.02 | 100.00 | 238.25 |

Example 7

Determining Plasma Profiles for Baclofen-containing Formulations

Figure 2:
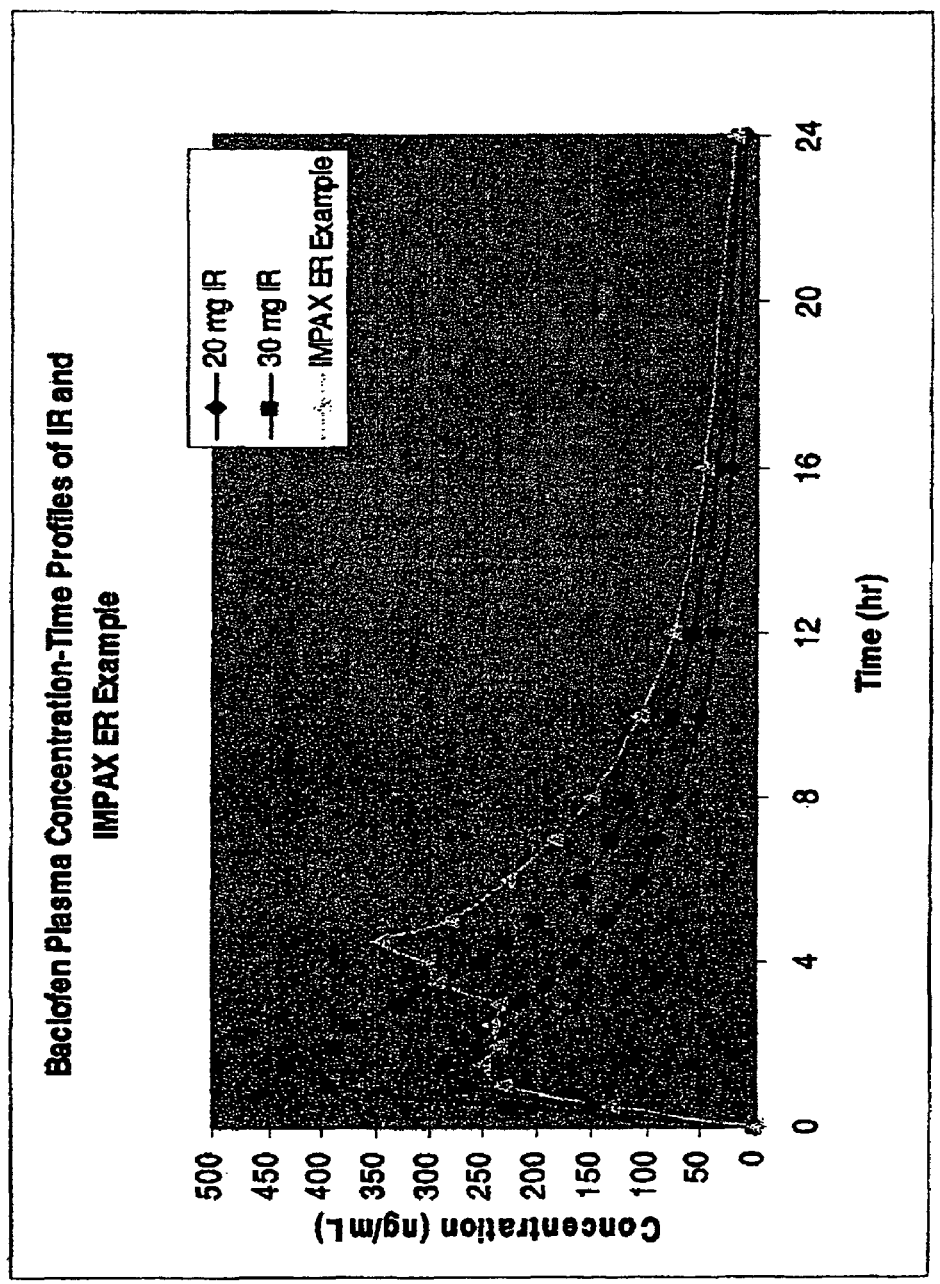
FIG. 2 is a graph of the in vivo plasma profiles of baclofen tablet formulations according to the protocol described in Example 7.

A bioavailability study was done in 20 healthy volunteers comparing a 36 mg baclofen formulation prepared according to Example 6, with the exception that the immediate-release component contained 12 mg baclofen and the enteric-coated controlled release component contained 24 mg baclofen, and the remaining excipients were adjusted dose proportionally. The formulation was compared with a 20 mg immediate release reference tablet (Watson Laboratories, Inc.) under fasting conditions. Test samples were administered orally with 240 ml of room temperature water after subjects are fasted overnight for at least 10 hours. No fluid, except that given with drug administration, is allowed from 1 hour prior to dose administration until 1 hour after dosing. At 2, 6, 8 and 12 hours post-dose, subjects consumed 240 ml of room temperature water. In addition, subjects consumed 480 ml of fluid with lunch and dinner. Blood samples were drawn at 0.5, 1, 1.5, 2, 2.5, 3, 3.5, 4, 4.5, 5, 6, 7, 8, 10, 12, 16, and 24 hours after administration. The results are shown in FIG. 2. In addition, FIG. 2 shows simulated blood plasma levels for 30 mg immediate-release baclofen, based on the data obtained from administration of the 20 mg dosage strength.

Example 8

Figure 3:
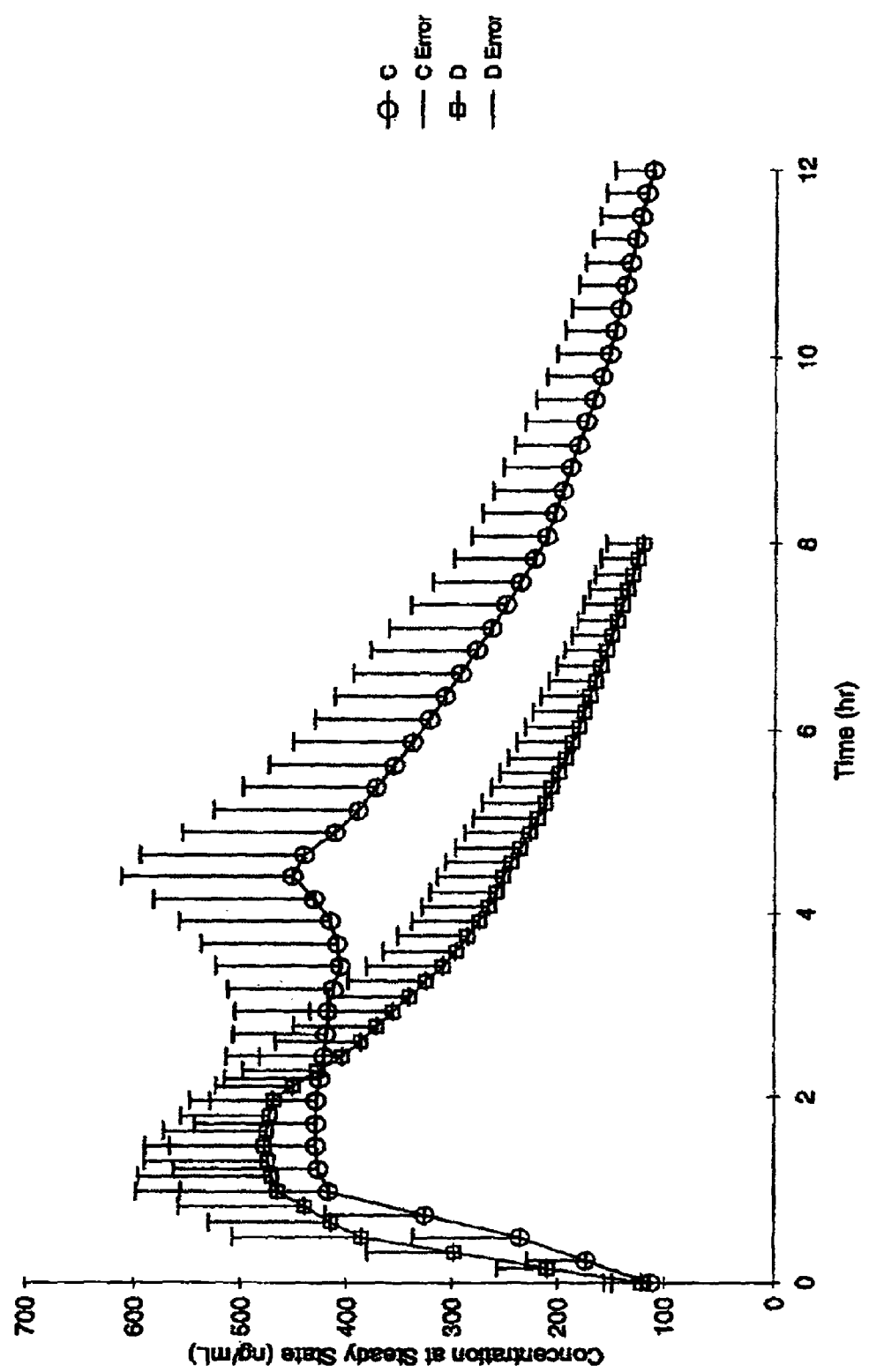
FIG. 3 is a graph simulating steady-state baclofen plasma levels according to the protocol described Example 8, where (C) represents the 40 mg dosage form of the present invention and (D) represents the reference 20 mg immediate-release dosage form.

Determining Steady State Plasma Profiles for Baclofen-containing Formulations Based on single-dose bioavailability data, steady-state mean baclofen plasma levels were calculated for a 40 mg baclofen formulation prepared according to Example 6 administered every 12 hours and an immediate-release 20 mg baclofen formulation (Watson Laboratories, Inc.) administered every 8 hours. The results are shown in FIG. 3 (where (C) represents the 40 mg dosage form of the present invention and (D) represents the reference 20 mg immediate-release dosage form). The results show that, at steady-state, the 40 mg dosage form of the present invention will reach a $C_{MIN}$ at 12 hours after administration comparable to the $C_{MIN}$ obtained by the immediate-release formulation eight hours after administration.

Having now fully described this invention, it will be understood to those of ordinary skill in the art that the methods of the present invention can be carried out with a wide and equivalent range of conditions, formulations, and other parameters without departing from the scope of the invention or any embodiments thereof.

What is claimed is:

1. A pharmaceutical dosage form of an absorption window active agent selected from the group consisting of baclofen, gabapentin, levodopa, α-methyldopa, valacyclovir, or a mixture of any thereof that exhibits prolonged absorption of the active agent in the small intestine comprising a plurality of controlled release particles, each particle comprising:
   i. the absorption window active agent selected from the group consisting of baclofen, gabapentin, levodopa, α-methyldopa, valacyclovir, or a mixture of any thereof;
   ii. an inner pH-sensitive polymer layer substantially enveloping the absorption window active agent; and
   iii. an outer pH-sensitive polymer layer substantially enveloping the absorption window active agent and inner pH-sensitive layer;
   wherein the dosage form provides prolonged absorption of the absorption window active agent in the small intestine, and wherein the outer pH-sensitive polymer layer dissolves at a lower pH than the inner pH-sensitive polymer layer.

2. The pharmaceutical dosage form of claim 1, wherein the outer pH-sensitive polymer layer dissolves at a pH of about 5.5 or higher and the inner pH-sensitive polymer layer dissolves at a pH of about 6 or higher.

3. The pharmaceutical dosage form of claim 1, further comprising an immediate release component.

4. The pharmaceutical dosage form of claim 3, wherein the immediate release component comprises immediate release particles.

5. The pharmaceutical dosage form of claim 1, further comprising a plasticizer.

6. The pharmaceutical dosage form of claim 5, wherein the plasticizer is selected from the group consisting of: 1,2-propylene glycol, acetylated monoglycerides, castor oil, dibutyl sebacate, diethyl phthalate, phthalate esters, polyethylene glycol, propylene glycol, triacetin, tributyl citrate, triethyl citrate, or a mixture of any thereof.

7. The pharmaceutical dosage form of claim 1, wherein the outer pH-sensitive polymer layer dissolves at a pH of about 3 or higher.

8. The pharmaceutical dosage form of claim 7, wherein the outer pH-sensitive polymer layer dissolves at a pH of about 4 or higher.

9. The pharmaceutical dosage form of claim 8, wherein the outer pH-sensitive polymer layer dissolves at a pH of about 4.5 or higher.

10. The pharmaceutical dosage form of claim 9, wherein the outer pH-sensitive polymer layer dissolves at a pH of about 5 or higher.

11. The pharmaceutical dosage form of claim 10, wherein the outer pH-sensitive polymer layer dissolves at a pH of about 5.5 or higher.

12. The pharmaceutical dosage form of claim 11, wherein the outer pH-sensitive polymer layer dissolves at a pH of about 6 or higher.

13. The pharmaceutical dosage form of claim 1, wherein the inner pH-sensitive polymer layer dissolves at a pH of about 5 or higher.

14. The pharmaceutical dosage form of claim 13, wherein the inner pH-sensitive polymer layer dissolves at a pH of about 5.5 or higher.

15. The pharmaceutical dosage form of claim 14, wherein the inner pH-sensitive polymer layer dissolves at a pH of about 6 or higher.

16. The pharmaceutical dosage form of claim 15, wherein the inner pH-sensitive polymer layer dissolves at a pH of about 6.5 or higher.

17. The pharmaceutical dosage from of claim 1, wherein the inner pH-sensitive polymer layer and/or the outer pH-sensitive polymer layer are comprised of pH-sensitive polymers selected from the group consisting of:
carboxymethylethylcellulose, cellulose acetate phthalate, cellulose acetate trimellitate, co-polymerized methacrylic acid, hydroxypropyl methylcellulose phthalate, methacrylic acid and methyl esters, polyvinyl acetate phthalate, or a mixture of any thereof.

18. The pharmaceutical dosage form of claim 17, wherein the outer pH-sensitive polymer layer comprises co-polymerized methacrylic acid.

19. The pharmaceutical dosage form of claim 3, wherein the ratio of the immediate release component to the controlled release component is from about 1:4 to about 4:1.

20. The pharmaceutical dosage form of claim 19, wherein the ratio of the immediate release component to the controlled release component is from about 1:2 to about 2:1.

21. The pharmaceutical dosage form of claim 1, wherein the absorption window active agent is in the amount of about 1 mg to about 1000 mg.

22. The pharmaceutical dosage form of claim 21, wherein the absorption window active agent is in the amount of about 1.5 mg to about 500 mg.

23. The pharmaceutical dosage form of claim 22, wherein the absorption window active agent is in the amount of about 2 mg to about 250 mg.

24. The pharmaceutical dosage form of claim 23, wherein the absorption window active agent is in the amount of about 2.5 mg to about 200 mg.

25. The pharmaceutical dosage form of claim 24, wherein the absorption window active agent is in the amount of about 10 mg to about 100 mg.

26. The pharmaceutical dosage form of claim 25, wherein the absorption window active agent is in the amount of about 15 mg to about 50 mg.

27. The pharmaceutical dosage form of claim 21, wherein the absorption window active agent is in the amount of about 300 mg to about 900 mg.

28. The pharmaceutical dosage form of claim 27, wherein the absorption window active agent is in the amount of about 400 mg to about 800 mg.

29. The pharmaceutical dosage form of claim 28, wherein the absorption window active agent is in the amount of about 450 mg to about 750 mg.

30. The pharmaceutical dosage form of claim 1, wherein the pharmaceutical dosage form is a tablet.

31. The pharmaceutical dosage form of claim 1, wherein the pharmaceutical dosage form is a capsule.

32. The pharmaceutical dosage form of claim 31, wherein the capsule further comprises discrete units selected from the group consisting of beads, granules, particles, tablets, or a mixture thereof.

33. The pharmaceutical dosage form of claim 1, wherein the absorption window active agent is baclofen.

34. The pharmaceutical dosage form of claim 33, wherein the baclofen is in the form of a prodrug, metabolite or pharmaceutically acceptable salt thereof.

35. The pharmaceutical dosage form of claim 1, wherein the absorption window active agent is a racemic mixture.

36. The pharmaceutical dosage form of claim 1, wherein the absorption window active agent is an optically pure isomeric mixture.

37. The pharmaceutical dosage form of claim 1, wherein the absorption window active agent is released in the stomach and small intestine.

38. The pharmaceutical dosage form of claim 1, wherein the baclofen is released in the upper small intestine.

39. The pharmaceutical dosage form of claim 1, wherein the baclofen is released in the duodenum.

40. The pharmaceutical dosage form of claim 1, wherein the baclofen is released in the jejunum.

41. The pharmaceutical dosage form of claim 1, wherein the outer polymer layer is present in an amount of about 5 weight percent to about 50 weight percent with respect to the particles.

42. The pharmaceutical dosage form of claim 41, wherein the outer polymer layer is present in an amount of about 15 weight percent to about 35 weight percent with respect to the particles.

43. The pharmaceutical dosage form of claim 1, wherein the inner polymer layer is present in an amount of about 5 weight percent to about 50 weight percent with respect to the particles.

44. The pharmaceutical dosage form of claim 43, wherein the outer polymer layer is present in an amount of about 20 weight percent to about 30 weight percent with respect to the particles.

45. The pharmaceutical dosage form of claim 1, wherein the inner pH-sensitive polymer layer envelops the particles and the outer pH-sensitive polymer layer envelops the particles and inner pH-sensitive layer.

* * * * *